(12) United States Patent  
Honda

(10) Patent No.: US 7,731,361 B2
(45) Date of Patent: Jun. 8, 2010

(54) OPHTHALMIC APPARATUS

(75) Inventor: Naoto Honda, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 33 days.

(21) Appl. No.: 12/155,222

(22) Filed: May 30, 2008

(65) Prior Publication Data

US 2008/0297722 A1 Dec. 4, 2008

(30) Foreign Application Priority Data

Jun. 4, 2007 (JP) .............................. 2007-148687

(51) Int. Cl.
*A61B 3/10* (2006.01)
(52) U.S. Cl. ..................... 351/211; 351/206; 351/208; 351/221
(58) Field of Classification Search ................. 351/211
See application file for complete search history.

(56) References Cited

U.S. PATENT DOCUMENTS

| | | | |
|---|---|---|---|
| 4,591,249 A | 5/1986 | Takahashi et al. | |
| 5,110,200 A * | 5/1992 | Snook | ................... 351/212 |
| 5,463,430 A | 10/1995 | Isogai et al. | |
| 5,909,268 A | 6/1999 | Isogai et al. | |
| 5,987,151 A * | 11/1999 | Akashi | ................... 382/100 |
| 6,382,796 B1 * | 5/2002 | Ban | ................... 351/212 |
| 6,409,343 B1 * | 6/2002 | Uchida | ................... 351/208 |
| 7,452,078 B2 * | 11/2008 | Isogai | ................... 351/205 |
| 2004/0207811 A1 | 10/2004 | Elsner | |
| 2005/0117116 A1 * | 6/2005 | Murakami | ................... 351/211 |
| 2006/0132711 A1 | 6/2006 | Iwanaga | |

FOREIGN PATENT DOCUMENTS

| | | |
|---|---|---|
| EP | 0 820 720 A1 | 1/1998 |
| EP | 1 316 287 A2 | 4/2003 |
| EP | 1 535 567 A1 | 6/2005 |
| JP | A 01-091831 | 4/1989 |
| JP | A 06-46999 | 2/1994 |
| JP | A 10-127581 | 5/1998 |

* cited by examiner

*Primary Examiner*—Jessica T Stultz
(74) *Attorney, Agent, or Firm*—Oliff & Berridge PLC

(57) ABSTRACT

An ophthalmic apparatus capable of performing alignment of the apparatus with respect to an examinee's eye with ease regardless of characteristics of the eye or an environment of the apparatus includes a measurement unit performing examination/measurement of the eye, a projection optical system for projecting an alignment target onto an anterior segment of the eye, an image-pickup optical system for picking up an anterior-segment image with an image of the projected target by a two-dimensional image-pickup element, and a calculation and control unit detecting the target image, and based on the detection result, detecting an alignment condition of the measurement unit with the eye, wherein the calculation and control unit detects two-dimensional luminance distribution in an image obtained by the element, and based on the detection result, changes projection light intensity of light of the target and/or gain of the element so that the target image becomes detectable.

4 Claims, 4 Drawing Sheets

OPHTHALMIC APPARATUS

BACKGROUND OF THE INVENTION

1. Field of the Invention

The present invention relates to an ophthalmic apparatus which performs examination or measurement of an examinee's eye.

2. Description of Related Art

There is known an ophthalmic apparatus such as a refractometer, a tonometer and a fundus camera, which performs examination or measurement of an examinee's eye, and the ophthalmic apparatus detects an alignment condition of the apparatus with respect to the eye by picking up an image of an alignment target in a spot shape, a ring shape or other shapes which is projected onto an anterior segment (a cornea) of the eye along with an image of the anterior segment by using a two-dimensional image-pickup element, and based on a result of the detection, automatically performs alignment of the apparatus with respect to the eye.

In such an apparatus, light of the alignment target often doubles as light for illuminating the anterior segment. For this reason, projection light intensity of the light of the alignment target and/or gain of the two-dimensional image-pickup element which picks up the alignment target image with the anterior-segment image are set to be higher in order to display the anterior-segment image brightly or to pick up the alignment target image clearly. However, if the projection light intensity of the light of the alignment target and/or the gain of the two-dimensional image-pickup element are set to be higher, there is a possibility that the alignment target image cannot be detected because of scattered light (noise light) from the anterior segment, depending on characteristics of the eye or an environment where the apparatus is placed. For example, if the eye has microcoria, the light of the alignment target (especially, the alignment target in the ring shape) is reflected and scattered by an iris of the eye and the scattered light enters the image-pickup element, which may have a detrimental effect on the detection of the alignment target image. In addition, if light intensity of extraneous light such as light of a light (illumination) in a room where the apparatus is placed is high, the extraneous light is reflected and scattered by the anterior segment and the scattered light enters the image-pickup element, which may have a detrimental effect on the detection of the alignment target image.

SUMMARY OF THE INVENTION

An object of the invention is to overcome the problems described above and to provide an ophthalmic apparatus which is capable of performing alignment of the apparatus with respect to an examinee's eye with ease regardless of characteristics of the eye or an environment where the apparatus is placed.

To achieve the objects and in accordance with the purpose of the present invention, an ophthalmic apparatus comprises a measurement unit arranged to perform examination or measurement of an examinee's eye, a projection optical system for projecting an alignment target in a predetermined shape onto an anterior segment of the eye, an image-pickup optical system for picking up an image of the anterior segment with an image of the projected alignment target by a two-dimensional image-pickup element, and a calculation and control unit arranged to detect the alignment target image based on an output signal from the image-pickup element, and based on a result of the detection, detect an alignment condition of the measurement unit with respect to the eye, wherein the calculation and control unit detects two-dimensional luminance distribution in an image obtained based on the output signal from the image-pickup element, and based on a result of the detection, changes projection light intensity of light of the alignment target and/or gain of the image-pickup element so that the alignment target image becomes detectable.

Additional objects and advantages of the invention are set forth in the description which follows, are obvious from the description, or may be learned by practicing the invention. The objects and advantages of the invention may be realized and attained by the ophthalmic apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
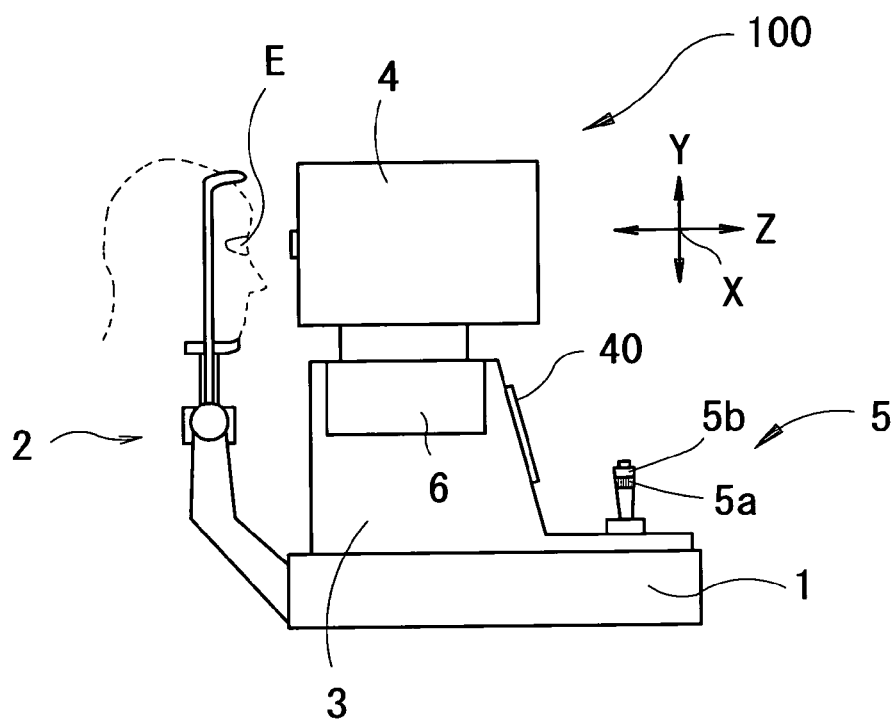
FIG. 1 is a view showing a schematic configuration of an ophthalmic apparatus according to a preferred embodiment of the present invention.

A detailed description of an ophthalmic apparatus according to a preferred embodiment of the present invention is provided below with reference to the accompanying drawings. FIG. 1 is a view showing a schematic configuration of an ophthalmic apparatus according to the preferred embodiment of the present invention. An ophthalmic apparatus 100 is a stationary ophthalmic apparatus which comprises a base 1, a face (head) support unit 2 mounted on the base 1, a mobile base 3 placed to be movable on the base 1, and a measurement unit (an examination unit) 4 placed to be movable on the mobile base 3. The measurement unit 4 houses an optical system to be described later. The mobile base 3 is moved on the base 1 in a right/left direction (hereinafter referred to as an "X-direction") and a back/forth direction (a working distance direction, hereinafter referred to as a "Z-direction") with respect to an examinee's eye E through tilting operation of a joystick 5. The measurement unit 4 is moved on the mobile base 3 in an up/down direction (hereinafter referred to as a "Y-direction") with respect to the eye E through rotational operation of a rotatable knob 5a. In addition, the measurement unit 4 is moved on the mobile base 3 in the X-, Y- and Z-directions with respect to the eye E by driving of a moving mechanism 6 provided on the mobile base 3. A measurement starting switch 5b is provided at the tip of the joystick 5. A monitor (a display) 40 is provided to the mobile base 3.

Figure 2:
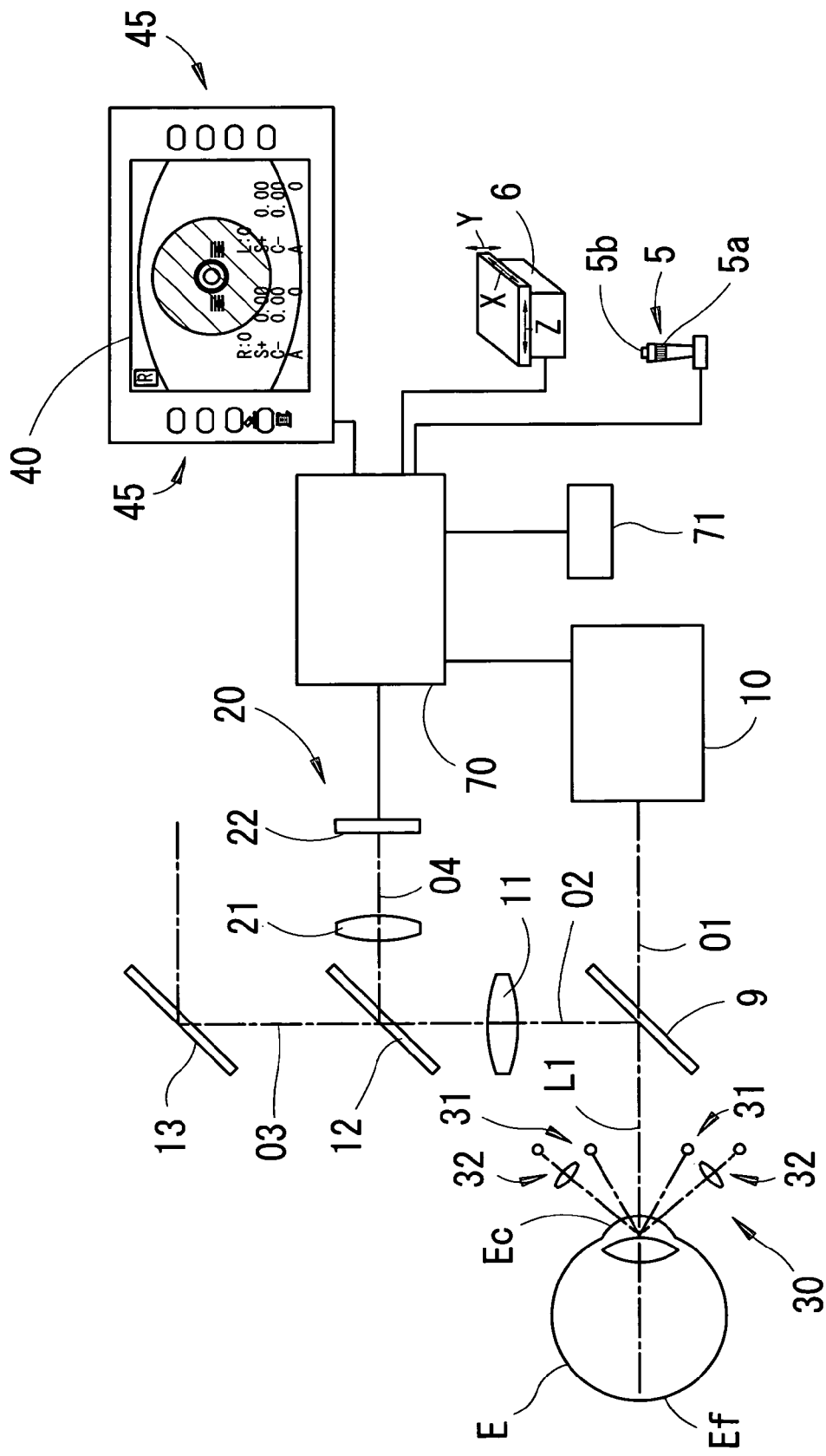
FIG. 2 is a view showing a schematic configuration of an optical system and a control system of the ophthalmic apparatus.

FIG. 2 is a view showing a schematic configuration of the optical system and a control system of the ophthalmic apparatus 100. An eye refractive power measurement optical system 10 is placed on an optical path O1 on which light transmitted through a dichroic mirror 9 travels, and the dichroic mirror 9 is placed in front of the eye E by moving the measurement unit 4 (and the mobile base 3). The measurement optical system 10 is an optical system for projecting a near infrared measurement target onto a fundus Ef of the eye E and picking up (photo-receiving) an image of the projected measurement target by an image-pickup element (a photo-detector) so as to obtain eye refractive power of the eye E based on an output signal from the image-pickup element.

On an optical path O2 on which light reflected by the dichroic mirror 9 travels, an objective lens 11 and a dichroic mirror 12 are placed. On an optical path O3 on which light transmitted through the dichroic mirror 12 travels, a total reflection mirror 13, and a fixation target projection optical system (not shown) for fixating the eye E on a fixation target are placed. On an optical path O4 on which light reflected by the dichroic mirror 12 travels, an observation optical system (an image-pickup optical system) 20 which comprises an image forming lens 21 and a two-dimensional image-pickup element 22 such as an area CCD placed in an almost conjugate position with the vicinity of an anterior segment of the eye E is placed.

An alignment target projection optical system 30 is placed in front of the eye E by moving the measurement unit 4 (and the mobile base 3). The projection optical system 30 comprises a projection optical system 31 for projecting a near infrared alignment target in a ring shape that is a target at a finite distance onto a cornea Ec of the eye E, and a projection optical system 32 for projecting near infrared alignment targets in a spot shape that are targets at an infinite distance onto the cornea Ec, and each of the projection optical system 31 and the projection optical system 32 is placed so as to be laterally symmetrical with respect to an optical axis L1 of the measurement optical system 10. The projection optical system 31 doubles as an optical system for illuminating the anterior segment. In the present preferred embodiment of the present invention, projection light intensity of light of the alignment target by the projection optical system 30 (31) is set to be higher so that an image of the anterior segment to be displayed on the monitor 40 (an observation image) appears bright as a whole.

The dichroic mirror 9 has a wavelength-selecting property of transmitting near infrared light emitted by a light source for projecting the measurement target included in the measurement optical system 10, and reflecting near infrared light emitted by light sources for projecting the alignment target (for illuminating the anterior segment) included in the projection optical system 30 and visible light (light of the fixation target). The dichroic mirror 12 has a wavelength-selecting property of transmitting the visible light, and reflecting the near infrared light.

An image of the anterior segment with images of the alignment targets projected by the projection optical system 30 is picked up by the image-pickup element 22.

A calculation and control unit 70 is connected with the light sources, the image-pickup element of the measurement optical system 10, the image-pickup element 22, a memory 71 which stores image data, measurement data and other data, the joystick 5, the rotatable knob 5a, the measurement starting switch 5b, the moving mechanism 6, the monitor 40, switches 45, and other members. The calculation and control unit 70 obtains the eye refractive power of the eye E based on the output signal from the image-pickup element of the measurement optical system 10. In addition, the calculation and control unit 70 controls the monitor 40 to display the anterior-segment image of the eye E based on an output signal from the image-pickup element 22.

Figure 3A:
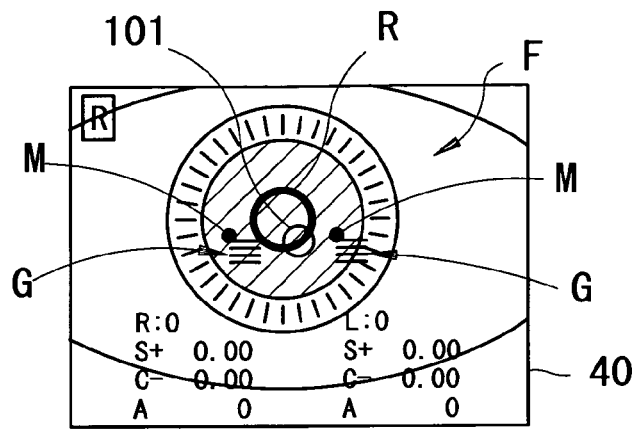
FIGS. 3A and 3B are views showing examples of images of an anterior segment of an examinee's eye and images of alignment targets which are displayed on a monitor.

Next, the operation of the apparatus having the above-described configuration will be described. A face (a head) of the examinee is supported by the support unit 2 and the eye E is fixated on the fixation target, and then alignment of the measurement unit 4 with respect to the eye E is performed so that the anterior-segment image is displayed on the monitor 40. Thus, an anterior-segment image F, a reticle mark 101, an alignment target image R in a ring shape (a Mayer ring image) which is projected by the projection optical system 31, alignment target images M in a spot shape which are projected by the projection optical system 32, and indicators G the number of which changes in order to indicate an alignment condition of the measurement unit 4 in the Z-direction with respect to the eye E are displayed on the monitor 40 (see FIG. 3A). The calculation and control unit 70 forms the reticle mark 101 and the indicators G and controls the monitor 40 to display them. The projection light intensity of the light of the alignment target is set to be higher enough than a saturation level of the sensitivity of the image-pickup element 22.

The calculation and control unit 70 detects an alignment condition of the measurement unit 4 with respect to the eye E by detecting the target images R and M based on the output signal from the image-pickup element 22. To be more specific, the alignment condition of the measurement unit 4 in the X- and Y-directions with respect to the eye E is obtained based on the center of the target image R. In addition, the alignment condition of the measurement unit 4 in the Z-direction with respect to the eye E is obtained based on a comparison between the space of the target image R and the space between the target images M (see U.S. Pat. No. 5,463,430 corresponding to Japanese Patent Application Unexamined Publication No. Hei06-46999). The calculation and control unit 70 detects the target images R and M by judging the present or absence of them in the image obtained by the image-pickup element 22 (the anterior-segment image) by subjecting the image to image processing such as pattern matching processing.

Figure 3B:
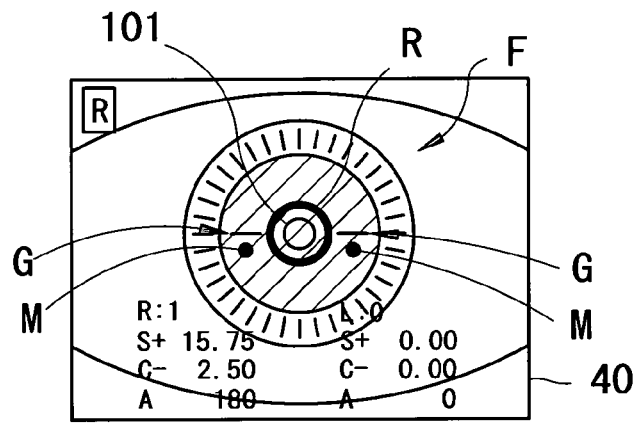

The calculation and control unit 70 moves the measurement unit 4 by controlling the driving of the moving mechanism 6 based on results of the detection of the alignment condition, and automatically performs the alignment of the measurement unit 4 with respect to the eye E. Then, upon completion of the alignment such that the target image R contains the reticle mark 101 and the number of indicators G displayed becomes one (see FIG. 3B), the calculation and control unit 70 automatically generates a trigger signal and starts measurement (examination). Besides, in the case of performing the automatic alignment, the calculation and control unit 70, for example, detects an alignment deviation amount of the measurement unit 4 with respect to the eye E by calculating a deviation amount between the center of the cornea Ec and an alignment reference position which is set at an intersection point of an image-pickup surface of the image-pickup element 22 and the measurement optical axis L1, and moves the measurement unit 4 so that the detected alignment deviation amount falls within a given permissible range. It is also preferable that the alignment of the measurement unit 4 with respect to the eye E is manually performed, and the calculation and control unit 70 judges the completion of the alignment based on the detection results of the alignment condition and automatically generates the trigger signal and starts the measurement. Alignment information maybe displayed on the monitor 40 based on the detection results of the alignment condition.

Figure 4:
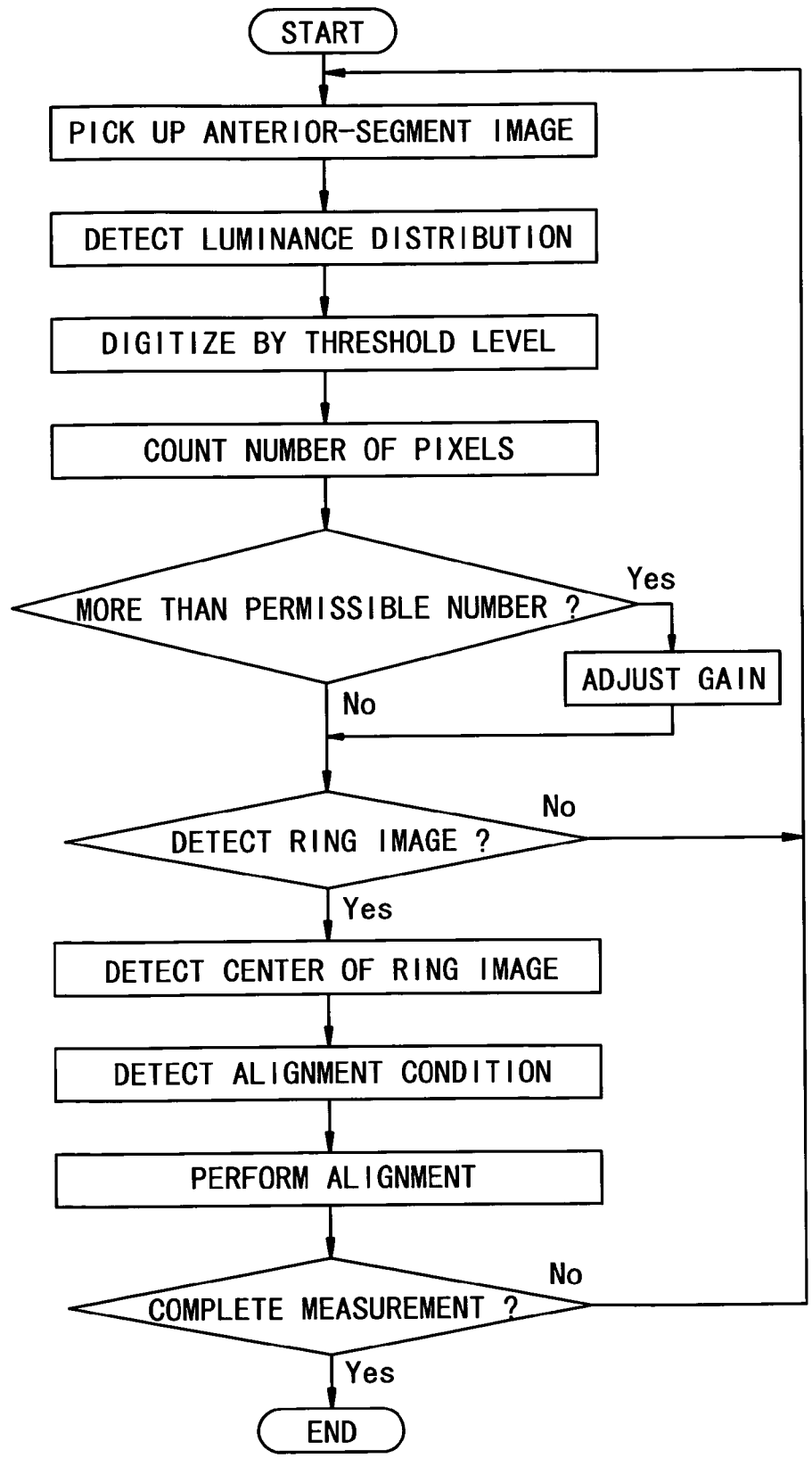
FIG. 4 is a flow chart showing operation of the apparatus in a case where scattered light from the anterior segment has an effect on detection of an alignment condition.

Hereinafter, a description of the operation in a case where scattered light (noise light) from the anterior segment has an effect on the above-described detection of the alignment condition will be provided referring to a flow chart of FIG. 4. Specifically, a description of the operation in a case where the eye E has a pupil of which the diameter is narrower (e.g., 1.8 mm) than that of the target image R (e.g., 2 mm) which is projected on the cornea Ec (i.e., the case of the eye E having microcoria) will be provided.

Figure 5:
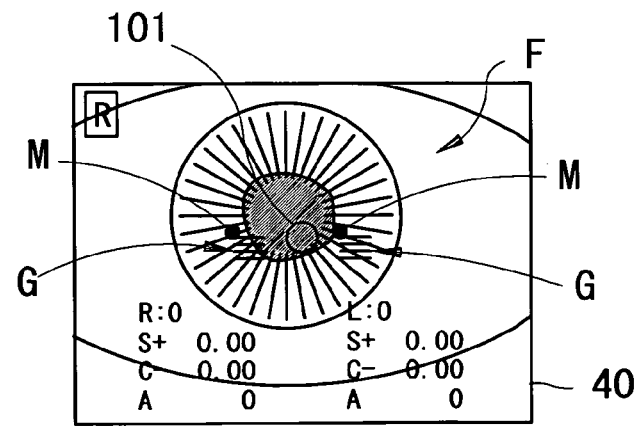
FIG. 5 is a view showing an example of an image of an anterior segment of an examinee's eye having microcoria and the alignment target images which are displayed on the monitor.

In this case, when the alignment is performed so that the anterior-segment image F is displayed on the monitor 40 (the anterior-segment image is picked up by the image-pickup element 22) as described above, a part (or all) of the light of the alignment target in the ring shape is reflected and scattered by an iris of the eye E and the scattered light enters the image-pickup element 22 (see FIG. 5).

Figure 6A:
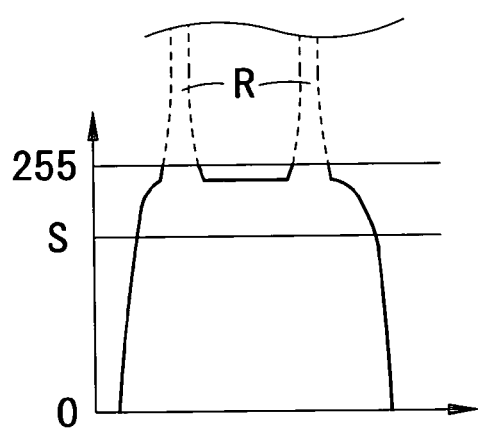
FIGS. 6A and 6B are views showing examples of luminance distribution in images obtained by a two-dimensional image-pickup element.
Figure 6B:
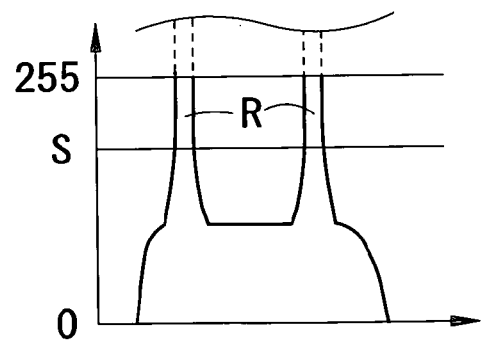

FIGS. 6A and 6B are views showing examples of distribution of luminance (level: 0 to 255) of pixels in the anterior-segment images F in a given horizontal direction. As a threshold level S used for detecting the target image R, a luminance value which is close to a midpoint between luminance around the target image R in the case of the little scattered light from the anterior segment and luminance at the saturation level in the image obtained by the image-pickup element 22 (level 255) is set. By using the threshold level S, the target image R can be detected with high precision. However, when the target image R falls on the iris as shown in FIG. 5, luminance of the scattered light from the iris becomes equal to the luminance of the target image R (the luminance at the saturation level) or goes beyond the threshold level S, and the presence or absence of the target image R cannot be judged because of the scattered light (see FIG. 6A), so that the calculation and control unit 70 cannot detect the target image R. Even if the target image R can be detected, there is a possibility that the detection is false.

In order to solve the above-described problem, the calculation and control unit 70 detects two-dimensional luminance distribution in the image obtained by the image-pickup element 22 (the anterior-segment image), and based on a result of the detection, changes gain of the image-pickup element 22 (gain of the output signal from the image-pickup element 22).

The calculation and control unit 70 scans image data two-dimensionally, which is stored in the memory 71 continuously at an image-pickup rate (a frame rate) of the image-pickup element 22, and detects thereby the luminance distribution in the entire image from luminance of each of pixels (or each of regions) in the image. In this case, a given luminance value is predetermined as a threshold level S, and a proportion of the luminance which goes beyond the threshold level S in the detected luminance distribution is obtained.

In the present preferred embodiment of the present invention, the calculation and control unit 70 detects the luminance distribution in the entire image, derives portions which go over the predetermined threshold level S (the same as the threshold level S used for detecting the target image R in the present preferred embodiment of the present invention) (i.e., digitizes the luminance distribution), and counts the number of pixels of which luminance goes over the threshold level S.

When the counted number of pixels is judged as being more than a given permissible number (a permissible range), the calculation and control unit 70 decreases the gain of the image-pickup element 22 by a given amount and detects the target image R. In addition, when the counted number of pixels is judged as being less than the permissible number, the calculation and control unit 70 detects the target image R without adjusting anything. For example, it is arranged that the number of pixels in a case where only the luminance of the target images R and M goes over the predetermined threshold level S is obtained as a reference number in advance, and when the counted number of pixels is in the vicinity of the reference number of pixels, or when it is assumed that the luminance has no effect on the alignment though the counted number of pixels is more than the reference number of pixels (when the counted number of pixels is two to four times as large as the reference number of pixels), the counted number of pixels is judged as being less than the permissible number. It is also preferable to predetermine the permissible number (the permissible range) to be larger in order to curb an effect of a change in the ring width of the target image R which is caused by the difference in curvature of the cornea Ec, the difference in the alignment condition of the measurement unit 4 in the Z-direction with respect to the eye E, or other factors.

The calculation and control unit 70 judges whether or not the target image R can be detected, and when the target image R can be detected, the calculation and control unit 70 detects the center of the target image R and detects the alignment condition of the measurement unit 4 in the X- and Y-directions with respect to the eye E, and then performs the automatic alignment. In addition, when the target images R and M can be detected, the calculation and control unit 70 detects the space of the target image R and the space between the target images M and detects the alignment condition of the measurement unit 4 in the Z-direction with respect to the eye E, and then performs the automatic alignment.

As described above, the calculation and control unit 70 repeats the control as mentioned above based on the image obtained by the image-pickup element 22 until the measurement is completed. In this case, the calculation and control unit 70 decreases the gain in stages at the image-pickup rate of the image-pickup element 22, and when the counted number of pixels of which the luminance goes over the threshold level S becomes less than the permissible number, adjustment of the gain is terminated. By decreasing the gain in stages as mentioned above, entire brightness of the anterior-segment image F displayed on the monitor 40 can be prevented from abruptly changing. If the counted number of pixels is still more than the permissible number even after the gain is decreased at a maximum, the calculation and control unit 70 assumes that the alignment condition is beyond detection and informs (displays) a message to recommend the manual alignment.

The gain is adjusted as described above, so that the target image R becomes detectable in the image obtained by the image-pickup element 22 (see FIG. 6B). The target image R can be detected even if the gain is decreased as mentioned above because the luminance of the target image R is remarkably larger than that of the scattered light (the noise light).

When the measurement is completed and a given measurement completion signal such as a signal to operate a print switch for printing out a measurement result is inputted, the calculation and control unit 70 resets the gain of the image-pickup element 22 to the initial state. It is also preferable that the gain of the image-pickup element 22 is reset to the initial state when the number of pixels of which the luminance goes over the threshold level S cannot be counted in the image obtained by the image-pickup element 22.

By having the above-described configuration, even if the projection light intensity of the light of the alignment target and/or the gain of the image-pickup element 22 are set to be higher in the alignment of the measurement unit 4 with respect to the eye E, the alignment condition can be detected with high precision.

In addition, the above-described configuration can be applied to a case where extraneous light reflected and scattered by the anterior segment and the scattered light (the noise light) enters the image-pickup element 22, a case where the light of the alignment target which is reflected and scattered by an opaque area of a cataractous eye and the scattered light (the noise light) enters the image-pickup element 22, and other cases. In other words, by adjusting the gain based on the detection of the two-dimensional luminance distribution in the image obtained by the image-pickup element 22, the target image R can be separated from a component of the scattered light (the noise light) in the anterior-segment image F.

Incidentally, a manner of detecting the two-dimensional luminance distribution in the image obtained by the image-pickup element 22 and judging whether or not to adjust the gain based on the detection result is not limited to the above-described manner. It is also preferable that whether or not an integrated value (a total sum) of the luminance of the pixels in the image obtained by the image-pickup element 22 is within a given permissible range is judged, or that whether or not an average value obtained by dividing the integrated value of the luminance of the pixels by the number of pixels is within a given permissible range is judged. It is essential only that whether or not the anterior-segment image (an image for alignment) includes the noise light to the extent of having an effect on the detection of the alignment condition be judged based on the two-dimensional luminance distribution in the entire anterior-segment image.

In addition, while the gain of the image-pickup element 22 is adjusted in the above-described descriptions, it is also preferable that the projection light intensity of the light of the alignment target by the projection optical system 30 (the projection optical system 31 and/or the projection optical system 32) is adjusted. However, in this case, the effect of the scattered light caused by the extraneous light reflected by the anterior segment cannot be curbed.

In addition, while the apparatus in the above-described descriptions is such that the alignment target in the ring shape is projected onto the cornea in order to detect the alignment condition of the apparatus (the measurement unit) in the X- and Y-directions with respect to the examinee's eye, the present invention can be also applied to an apparatus such that an alignment target in a spot shape is projected onto the cornea from the front of the examinee's eye (e.g., an apparatus such that a bright point is formed at a corneal vertex). In this case, it is possible that the calculation and control unit detects the size of an image of the alignment target, and based on a result of the detection, changes the projection light intensity of the light of the alignment target and/or the gain of the image-pickup element. To be more specific, it is possible that when the size of the alignment target image at the time when the luminance distribution is digitized by a given threshold level is larger than a given permissible size, the gain of the image-pickup element can be decreased so that the size of the alignment target image at the time of the digitization is made smaller. By doing this, a degree of precision of the detection of the alignment target image can be improved even when the examinee's eye has opacity within its pupil and scattered light is generated thereby.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An ophthalmic apparatus comprising:
   a measurement unit arranged to perform one of examination and measurement of an examinee's eye;
   a projection optical system included in the measurement unit and comprising a light source, which is arranged to project an infrared alignment target onto an anterior segment of the eye;
   an image-pickup optical system included in the measurement unit and comprising a two-dimensional image-pickup element having a sensitivity in at least an infrared range, which is arranged to pick up an image of the anterior segment with an image of the projected alignment target by the image-pickup element; and
   a calculation and control unit arranged to obtain the anterior segment image based on an image signal from the image-pickup element, detect the alignment target image, and based on a result of the detection, detect an alignment condition of the measurement unit with respect to the eye, wherein
   the calculation and control unit obtains luminance distribution of the image signal from the image-pickup element, judges whether or not the number of pixels or an integral value of which luminance goes over a threshold level is more than a given permissible range, and when the judgment is affirmative, decreases at least one of light intensity of the alignment target and gain of the image signal from the image-pickup element.

2. The ophthalmic apparatus according to claim 1, wherein the calculation and control unit decreases at least one of the light intensity and the gain in stages at an image-pickup rate of the image-pickup element.

3. The ophthalmic apparatus according to claim 1, wherein the light source for alignment target projection is arranged to double as a light source for illuminating the anterior segment illumination.

4. An ophthalmic apparatus comprising:
   a measurement unit arranged to perform one of examination and measurement of an examinee's eye;
   a projection optical system included in the measurement unit and comprising a light source, which is arranged to project an infrared alignment target onto an anterior segment of the eye;
   an image-pickup optical system included in the measurement unit and comprising a two-dimensional image-pickup element having a sensitivity in at least an infrared range, which is arranged to pick up an image of the anterior segment with an image of the projected alignment target by the image-pickup element; and
   an alignment condition detection means arranged to obtain the anterior segment image based on an image signal from the image-pickup element, detect the alignment target image, and based on a result of the detection, detect an alignment condition of the measurement unit with respect to the eye, and an alignment control means arranged to obtain luminance distribution of the image signal from the image-pickup element, judge whether or not the number of pixels or an integral value of which luminance goes over a threshold level is more than a given permissible range, and when the judgment is affirmative, decrease at least one of light intensity of the alignment target and gain of the image signal from the image-pickup element.

* * * * *